United States Patent [19]

Kimura et al.

[11] 4,347,114
[45] Aug. 31, 1982

[54] FLAT THIN FILM TYPE OXYGEN SENSOR

[75] Inventors: Shinji Kimura, Yokohama; Hiroshi Takao, Kamakura; Satoshi Ambe, Yokosuka; Yoshio Akimune, Yokohama, all of Japan

[73] Assignee: Nissan Motor Co., Ltd., Yokohama, Japan

[21] Appl. No.: 162,001

[22] Filed: Jun. 23, 1980

[30] Foreign Application Priority Data

Jun. 26, 1979 [JP] Japan ................................. 54-79736

[51] Int. Cl.$^3$ .............................................. G01N 27/58
[52] U.S. Cl. ................................................ 204/195 S
[58] Field of Search .......................... 204/195 S, 1 S

[56] References Cited

U.S. PATENT DOCUMENTS

| | | | |
|---|---|---|---|
| 3,503,809 | 3/1970 | Spacil | 204/195 S X |
| 3,719,564 | 3/1973 | Lilly et al. | 204/1 T |
| 3,843,400 | 10/1974 | Radford et al. | 204/195 S X |
| 4,021,326 | 5/1977 | Pollner et al. | 204/195 S |
| 4,040,929 | 8/1977 | Bauer et al. | 204/195 S |
| 4,119,512 | 10/1978 | Inoue et al. | 204/195 S |
| 4,207,159 | 6/1980 | Kimura et al. | 204/195 S |
| 4,265,724 | 5/1981 | Haecker et al. | 204/195 S |

FOREIGN PATENT DOCUMENTS

| | | |
|---|---|---|
| 2742278 | 3/1978 | Fed. Rep. of Germany . |
| 2746381 | 4/1978 | Fed. Rep. of Germany . |
| 2718907 | 11/1978 | Fed. Rep. of Germany ... 204/195 S |
| 2830778 | 1/1980 | Fed. Rep. of Germany ... 204/195 S |
| 3019824 | 11/1980 | Fed. Rep. of Germany ... 204/195 S |
| 1582347 | 9/1969 | France . |
| 2350598 | 12/1977 | France . |
| 2428840 | 1/1980 | France . |
| 1479151 | 7/1977 | United Kingdom ............ 204/195 S |

*Primary Examiner*—G. L. Kaplan
*Attorney, Agent, or Firm*—Schwartz, Jeffery, Schwaab, Mack, Blumenthal & Koch

[57] ABSTRACT

In an oxygen sensor comprising an oxygen ion conductive solid electrolyte, an electronically conductive reference electrode layer formed on one side of the electrolyte layer, an electronically conductive measurement electrode layer formed on the other side of the electrolyte layer, and a partition layer of an electrochemically inactive material formed on the outer side of the reference electrode layer, at least one of the reference and measurement electrode layers has a plurality of openings through which two layers which put therebetween the one of the electrode layers are united with each other.

6 Claims, 21 Drawing Figures

FLAT THIN FILM TYPE OXYGEN SENSOR

BACKGROUND OF THE INVENTION

The present invention relates in general to an oxygen sensor for measuring the oxygen concentration in a fluid, the sensor being of the type having a layer of an oxygen ion conductive solid electrolyte. More specifically, the present invention is concerned with a so-called flat thin film type oxygen sensor which is suitable for measuring the oxygen concentration in an engine exhaust gas.

It is known that the flat thin film type oxygen sensors using a flat thin film solid electrolyte show better performance in EMF (electromotive force) characteristic and responsiveness as compared with tubular type oxygen sensors which use a tubular solid electrolyte. Some of these sensors have however a poor durability. In fact, it often happens that mutually attached element layers which form the thin film oxygen sensor come off or peel off from one another during the practical usage thereof.

SUMMARY OF THE INVENTION

According to the present invention, there is provided an oxygen sensor. The sensor comprises an oxygen ion conductive solid electrolyte layer, and electronically conductive reference electrode layer formed on one side of the electrolyte layer, an electronically conductive measurement electrode layer formed on the other side of the electrolyte layer, and a partition layer of an electrochemically inactive material formed on the outer side of the reference electrode layer. The oxygen sensor is characterized in that at least one of the reference and measurement electrode layers has a plurality of openings through which two layers which put therebetween the one of the electrode layers are united with each other.

It is an object of the present invention to provide a flat thin film type oxygen sensor which has excellent durability.

It is another object of the present invention to provide a flat thin film type oxygen sensor which is suitable for measuring the oxygen concentration in an exhaust gas emitted from an automotive internal combustion engine.

Other objects and advantages of the present invention will become clear from the following description when taken in conjunction with the accompanying drawings.

DESCRIPTION OF PRIOR ART OXYGEN SENSOR

Prior to describing in detail the oxygen sensor of the invention, an outline explanation of one of conventional flat thin film type oxygen sensors such as one shown in FIG. 1 will be made in order to clarify the present invention.

Figure 1:
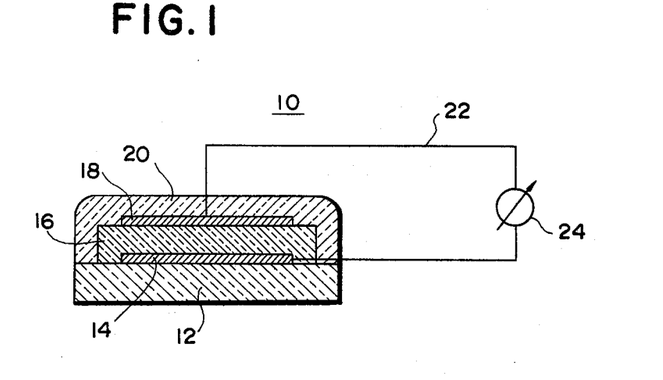
FIG. 1 is a cross section view of a conventionally used flat thin film type oxygen sensor.

Referring to FIG. 1, the side cross section of the conventional oxygen sensor is designated by reference numeral 10. The sensor 10 generally comprises a partition layer 12 of ceramics designed to serve as a structural base member of the sensor, a first or reference electrode layer 14 deposited on the partition layer 12, a layer 16 of an oxygen ion conductive solid electrolyte deposited on the first electrode layer 14, a second or measurement electrode layer 18 deposited on the solid electrolyte layer 16, and a protective layer 20 entirely and intimately covering both the second electrode layer 18 and side surfaces of the solid electrolyte layer 16, as shown. The protective layer 20 has a porous or gas permeable structure. Leads 22 are connected via a potentiometer 24 to the first and second electrode layers to permit the potentiometer 24 to measure the electromotive force (EMF) generated between the electrode layers 14 and 18. The partition layer 12 is constructed of a sintered body of alumina ($Al_2O_3$). Platinum (Pt) is used for the electrode layers 14 and 18. Yttria stabilized zirconia ($Y_2O_3$-$ZrO_2$) or calcia stabilized zirconia (CaO-$ZrO_2$) is used as the material of the solid electrolyte layer 16. Calcium zirconate (CaO-$ZrO_2$) or alumina ($Al_2O_3$) is used for the material of the protective layer 20.

In this type oxygen sensor 10, the following four regions form independently a so-called metal-ceramic boundary surface or metal-ceramic interface:

(1) the region defined between the partition layer 12 and the first electrode layer 14;

(2) the region defined between the first electrode layer 14 and the solid electrolyte layer 16;

(3) the region defined between the solid electrolyte layer 16 and the second electrode layer 18;

(4) the region defined between the second electrode layer 18 and the protective layer 20.

Observation of these interfaces by scanning electron microscope has revealed that the bond occuring at those regions is not made by chemical adhesion, but physical adhesion or mechanical ahhesion, which means that the bond at those regions is not strongly made. In fact, it often happens that the attached layers 14, 16, 18 and 20 on the partition layer 12 come off or peel off from one another during the practical use of the sensor mainly because of different heat expansion rate of these layers. This unwanted phenomenon becomes more critical when such sensor is installed in an automotive engine exhaust system. Under this circumstance, the sensor must endure not only high temperature of the exhaust gas, but also high speed flow of the same.

DESCRIPTION OF THE EMBODIMENTS OF THE INVENTION

Throughout the following description, like parts are designated by the same reference numerals.

Figure 2:
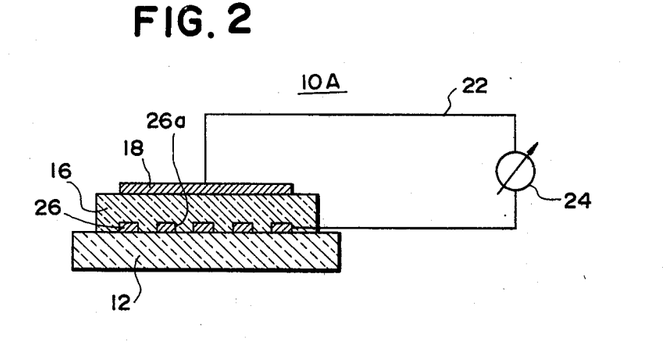
FIGS. 2 to 6 are views similar to FIG. 1, but showing respectively the embodiments of the present invention.

Referring to FIG. 2 of the drawings, there is shown an oxygen sensor according to the first embodiment, which is designated by reference 10A. The oxygen sensor 10A comprises a partition layer 12 of ceramics which is designed to serve as a structural base member of the sensor 10A. A grid-shaped first or reference electrode layer 26 having a plurality of rectangular openings 26a is deposited on the partition layer 12, and a layer 16 of an oxygen ion conductive solid electrolyte is deposited on the first electrode layer 26. A second or measurement electrode layer 18 is deposited on the electrolyte layer 16. Similarly to the case of FIG. 1, leads 22 are connected via a potentiometer 24 to the first and second electrode layers 26 and 18. It should be noted that the electrode layers 26 and 18 and the solid electrolyte layer 16 have a microscopically porous structure, i.e. a gas permeable structure, while the partition layer 12 has a structure impervious to gas.

Figure 3:
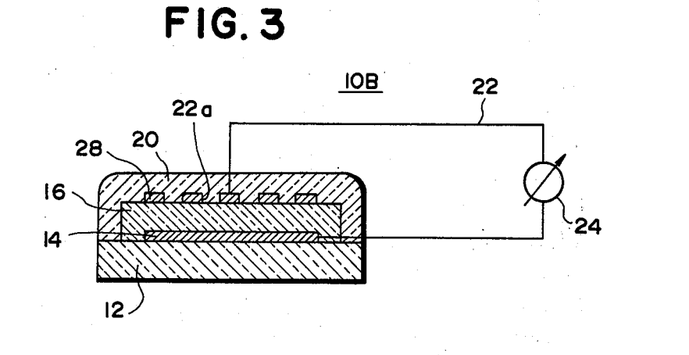

Referring to FIG. 3, there is shown the second embodiment of the invention. The oxygen sensor 10B of this embodiment comprises a partition layer 12 serving as a structural base member of the sensor 10B, a first electrode layer 14 deposited on the partition layer 12, a layer 16 of an oxygen ion conductive solid electrolyte deposited on the first electrode layer 14, a grid-shaped second electrode layer 28 having a plurality of rectangular openings 28a formed therein deposited on the electrolyte layer 16, and a protective layer 20 entirely and intimately covering both the second electrode layer 28 and side surfaces of the solid electrolyte layer 16. Leads 22 and a potentiometer 24 are arranged in the same manner as in the case of the first embodiment.

Figure 4:
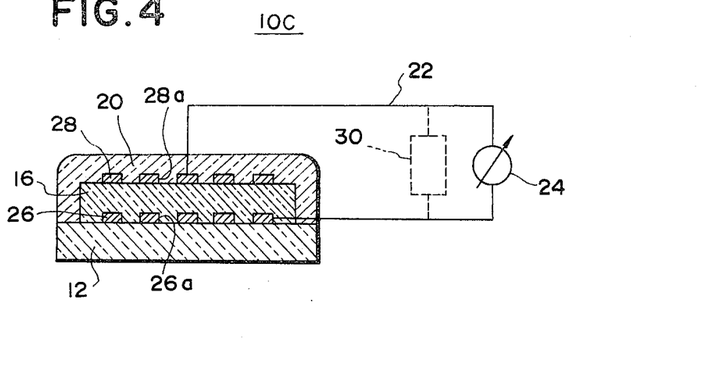

Referring to FIG. 4, the third embodiment is shown. The oxygen sensor 10C of this embodiment comprises a partition layer 12 serving as the structural base member of the sensor 10C, a grid-shaped first electrode layer 26 having a plurality of rectangular openings 26a formed therein deposited on the partition layer 12, a layer of an oxygen ion conductive solid electrolyte 16 deposited on the first electrode layer 26, a grid-shaped second electrode layer 28 having a plurality of rectangular openings 28a formed therein deposited on the electrolyte layer 16, and a protective layer 20 entirely and intimately covering both the second electrode layer 28 and side surfaces of the electrolyte layer 16. Leads 22 and a potentiometer 24 are arranged in the same manner as in the case of the first embodiment.

If desired, a DC power source 30 (preferably a constant current DC power source) may be connected in parallel with the potentiometer 24 in a manner as indicated by broken lines to enforcedly cause a DC current to flow from one side of the solid electrolyte layer 16 to the other side. Addition of such DC power source 30 stabilizes the oxygen partial pressure appearing at the interface between the first electrode layer 26 and the solid electrolyte layer 16.

Figure 5:
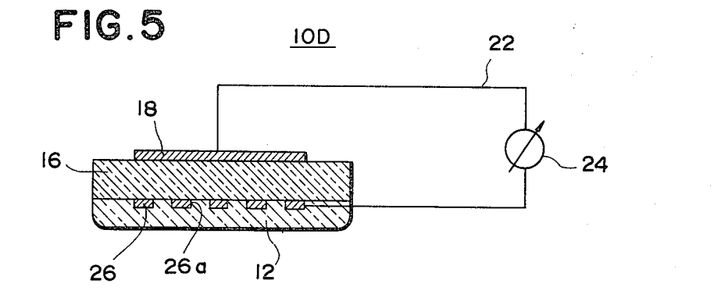

Referring to FIG. 5, the fourth embodiment of the invention is shown. The oxygen sensor 10D of this embodiment comprises a layer 16 of an oxygen ion conductive solid electrolyte which is designed to serve as the structure base member of the sensor 10D. A grid-shaped first electrode layer 26 having a plurality of rectangular openings 26a is deposited on the lower surface of the solid electrolyte layer 16 and a partition layer 12 is deposited on the first electrode layer 26. A second electrode layer 18 is deposited on the upper face of the solid electrolyte layer 16. Leads 22 and a potentiometer 24 are arranged in the same manner as in the case of the first embodiment.

Figure 6:
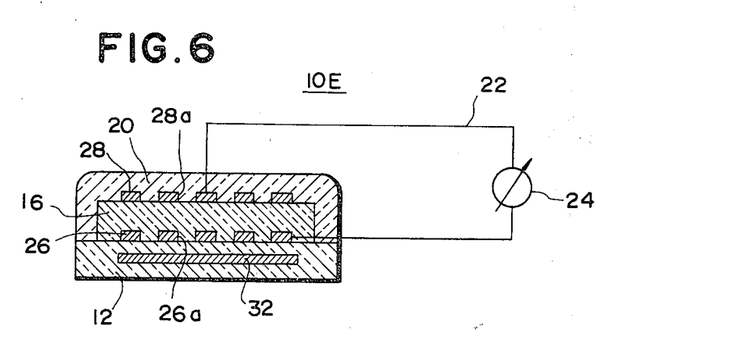

Referring to FIG. 6, the fifth embodiment of the invention is shown. The oxygen sensor 10E of this embodiment comprises substantially the same parts as in the case of the third embodiment of FIG. 4 except that in this fifth embodiment, an electrically conductive heating layer 32 is embedded in the partition layer 12. By applying the heating layer 32 with an electric power for generation of heat therefrom, the oxygen ion conductivity of the solid electrolyte layer 16 is considerably improved. In fact, the oxygen ion conductivity of the electrolyte layer 16 is poor at low temperature. Thus, the oxygen sensor which includes such heating layer 32 is particularly suitable for measuring the oxygen concentration in a low temperature gas. In view of a fact that an automotive engine issues a low temperature exhaust gas at its starting employment of such oxygen sensor 10E in the exhaust system of the engine is desirable.

Now, it should be noted that the electrode layer 26 or 28 is not limited to a grid-shaped article having regularly arranged rectangular openings. In other words, the electrode layer 26 or 28 may have any configuration so long as it has through openings through which adjacent two ceramic layers (for example: the partition layer 12 and the solid electrolyte layer 16, or for example: the solid electrolyte layer 16 and the protective layer 20) are united with each other. Thus, each of the through openings may be of the circular, triangular or quadrate form.

As will become more apparent hereinafter, several experiments have revealed that using the above-mentioned perforated electrically conductive layer as at least one of the electrode layers of the sensor permits the sensor to have excellent durability. This is because the mechanical bond between adjacent two layers (such as: the partition layer and the first electrode layer, the first electrode layer and the solid electrolyte layer, the solid electrolyte layer and the second electrode layer, or the second electrode layer and the protective layer) is reinforced by strong ceramic-ceramic bonding achieved between the adjacent ceramic layers through the openings of the perforated electrode layer. In fact, at the interface defined by the adjacent ceramic layers through the openings of the electrode layer, there occurs diffusion of atoms or ions, which means formation of chemical or strong adhesion between the adjacent ceramic layers.

Further, it has been revealed that addition of proper amounts of components of the partition layer 12 (or the electrolyte layer 16) to the first electrode layer 26 to form an electrically conductive cermet electrode layer increases the bonding force appearing at the interface between the partition layer 12 and the first electrode layer 26 (or the interface between the first electrode layer 26 and the electrolyte layer 16), and addition of proper amounts of components of the electrolyte layer 16 (or the protective layer 20) to the second electrode layer 28 to form an electrically conductive cermet electrode layer also increases the bonding force appearing at the interface between the electrolyte layer 16 and the second electrode layer 28 (or the interface between the second electrode layer 28 and the protective layer 20). Furthermore, it has been revealed by experiments that if the partition layer 12, the first electrode layer 26 or 14, the electrolyte layer 16, and the second electrode layer 28 or 18 (and the protective layer 20, if provided) are orderly heaped or layered on one another in green conditions thereof and then the thus temporarily bonded layers are baked or fired at the same time, the durability of the oxygen sensor thus produced is much more improved.

It has been also revealed that when the cermet electrode layers are used, the preferable mixing ratio of the ceramic and the metal for forming the cermet is given by the next equation:

$$\frac{\text{volume of the ceramic used}}{\text{volume of the cermet produced}} \times 100 \leq 30\% \quad (1)$$

This equation is backed up by a phenomenon in which if the ceramic-cermet volume ratio is greater than 30%, the electron conductivity of the produced cermet is greatly lowered.

In the oxygen sensor of the present invention, it is suitable to use as the material of the partition layer 12 an electrically nonconductive inorganic material such as alumina, mullite, spinel or forsterite. Further, it is also possible to use as the material of the partition layer 12 a cermet. In case of the partition layer 12 being a structural base member of the oxygen sensor, it is possible to use either a moulded compressed powder article of the above-mentioned materials or a cut piece such as a piece which is provided by cutting a ceramic slip. In case of the solid electrolyte layer 16 being a structural base member of the oxygen sensor, the partition layer 12 can be produced by dipping method, printing method or plasma spraying method.

As the material of the oxygen ion conductive solid electrolyte layer 16, $ZrO_2$ stabilized with CaO, $Y_2O_3$, SrO, MgO, $ThO_2$, $WO_3$ or $Ta_2O_5$; $Bi_2O_3$ stabilized with $Nb_2O_5$, SrO, $WO_3$, $Ta_2O_5$ or $Y_2O_3$; and $Y_2O_3$ stabilized with $ThO_2$ or CaO are usable in the present invention. When the partition layer 12 is constructed to serve as the structural base member of the oxygen sensor, the solid electrolyte layer 16 may take the form of a thin film deposited on the partition layer 12 by sputtering, vacuum evaporation or an electrochemical process, or by firing or baking a solid electrolyte paste applied onto the partition layer 12. When the solid electrolyte layer 16 is made to be a structural base member of the sensor, it is possible to use a moulded compressed powder article of the above-mentioned materials.

The first electrode layer 14 or 26 and the second electrode layer 18 or 28 are each made of a material selected from electrode materials for conventional oxygen sensors utilizing a solid electrolyte. Examples are Au, Ag and SiC which do not exhibit any catalytic action on oxidation reactions and catalytic metals such as Ru, Pd, Rh, Os, Ir and Pt, including alloys of these platinum group metals and alloys of a platinum group metal with a base metal. Preferably, such electrode layers 14, 26, 18 and 28 are each made of a cermet which is provided by sintering the above-mentioned metals of the alloys with a ceramic material. The ceramic material is preferably selected from the materials which form the partition layer 12, the solid electrolyte layer 16 or the protective layer 20 for the reason mentioned hereinbefore. The electrode layers 14, 26, 18 and 28 are formed by sputtering, vacuum evaporation, an electrochemical process or firing of a metal powder paint or paste.

When a porous protective layer 20 for protecting the second electrode layer 28 is employed as in cases of FIGS. 3 and 4, such layer 20 is made of alumina, mullite, spinel or calcium zirconate ($CaO-ZrO_2$ system) and can be formed by wetting the second electrode layer 28 with an aqueous dispersion of such an oxide material and baking the wetted article, or by plasma spraying of the oxide material.

When an electrically conductive heating layer 32 is employed as in case of FIG. 6, such layer 32 is made of a resistive metal such as Pt, W or Mo and can be formed by baking a metal powder paste embedded in the partition layer 12.

The present invention will be further illustrated by the following examples.

EXAMPLE 1

As an example of the oxygen sensor of the present invention, an oxygen sensor having the constructions of the sensor 10A shown in FIG. 2 and the protective layer 20 was produced. The production process is illustrated in FIGS. 7a to 7g of the drawings. For ease of description, the oxygen sensor of this example will be designated by 10A-1.

Figure 7A:
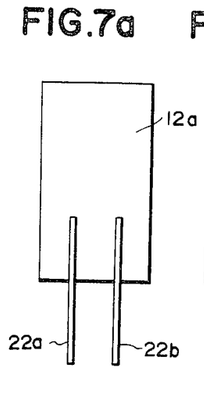
FIGS. 7a to 7g are views depicting, in order, the production process of an oxygen sensor according to the present invention.
Figures 7B, 7C, 7D:
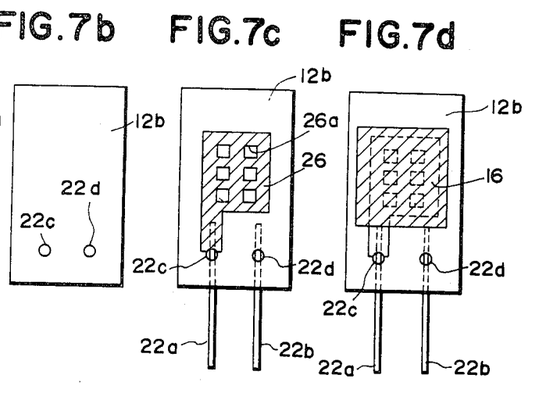
Figures 7E, 7F, 7G:
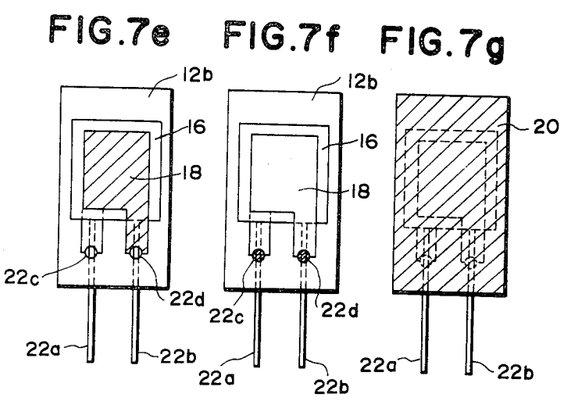

To produce such sensor, a pair of platinum wires 22a and 22b (0.2 mm in diameter and 10 mm in length, each) were placed on an alumina green sheet 12a (9 mm in length, 5 mm in width, 0.7 mm in thickness) in a manner shown in FIG. 7a. As is shown by FIG. 7b, another alumina green sheet 12b (of the identical size of the sheet 12a) having a pair of through holes 22c and 22d formed therein was placed on the green sheet 12a to put therebetween the wires 22a and 22b and then these two green sheets 12a and 12b were pressed against each other. Then, a platinum paste composed of 70 wt % powdered platinum and 30 wt % organic medium (such as lacquer thinner) was applied or painted onto a major portion of the outer face of the green sheet 12b in a manner to form a grid-shaped paste heap or layer on the green sheet 12b, the heap or layer having an extension extending to the hole 22c as is illustrated in FIG. 7c, then the paste heap or layer was air-dried to form an unbaked first electrode layer 26. The thickness of the dried layer 26 was about 6 to 7 μm. Then, an electrolyte paste composed of 70 wt % powdered $Y_2O_3$-$ZrO_2$ (1:19 mole ratio) and 30 wt % organic medium (such as lacquer thinner) was applied or painted onto the dried grid-shaped layer 26 so that the peripheral portion of the painted electrolyte paste 16 extends to the outer face of the green sheet 12b, as is understood from FIG. 7d, and the paste 16 was air-dried to form an unbaked solid electrolyte layer 16. The thickness of the dried layer 16 was about 10 to 12 μm. Then the same platinum paste as that forming the grid-shaped layer 26 was applied or painted onto the dried electrolyte paste 16 in such a manner that an extension of the painted platinum paste extends to the hole 22d, as shown in FIG. 7e, and at the same time the platinum paste was applied to the through holes 22c and 22d as shown in FIG. 7f. Then the platinum paste thus applied was air-dried to form an unbaked second electrode layer 18. The thickness of the dried layer 18 was about 6 to 7 μm. Then, the unbaked multi-layered article thus produced was baked in air for 2 hours at a temperature of about 1500° C. After this process, powdered calcium zirconate ($CaO-ZrO_2$ system) was deposited on the entire front face of the baked multi-layered article by plasma spraying technique to form a porous protective layer 20, as is depicted by FIG. 7g. The thickness of the protective layer 20 thus produced was about 80 to 100 μm.

EXAMPLE 2

The oxygen sensor 10B of FIG. 3 was produced in this example. The production process is depicted in part by FIGS. 9a to 9c. The green-conditioned partition layer 12 was produced by employing the same technique as in the case of the example 1. A platinum paste composed of 70 wt % powdered platinum and 30 wt % organic medium (such as lacquer thinner) was applied or painted onto the partition layer 12 and air-dried to form an unbaked first electrode layer 14. The thickness of the dried layer 14 was about 6 to 7 μm. Then, an electrolyte paste composed of 70 wt % powdered $Y_2O_3$-$ZrO_2$ (1:19 mole ratio) and 30 wt % organic medium (such as lacquer thinner) was applied or painted onto the dried layer 14 and then air-dried to form an unbaked solid electrolyte layer 16.

Figure 9A:
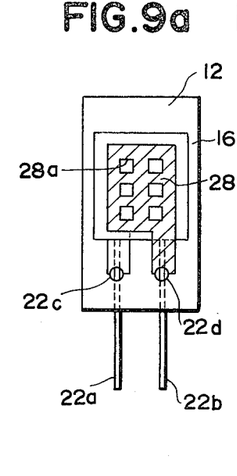
FIGS. 9a to 9c are views depicting, in order, the production process of another oxygen sensor according to the present invention.
Figures 9B, 9C:
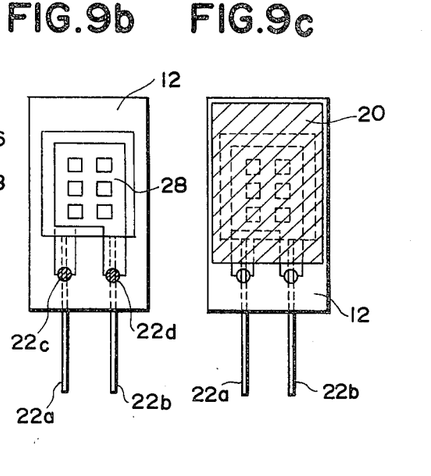

The thickness of the dried layer 16 was about 10 to 12 μm. Then the same platinum paste as that forming the first electrode layer 14 was applied or painted onto the dried electrolyte paste layer 16 in a manner to form a grid-shaped paste heap or layer thereon, as is depicted in FIG. 9a, and at the same time the platinum paste was applied to the through holes 22c and 22d as shown in FIG. 9b. Then, the platinum paste thus applied was air-dried to form an unbaked second electrode layer 28. The thickness of the dried layer 28 was about 6 to 7 μm. Then, an alumina paste composed of 70 wt % powdered alumina and 30 wt % organic medium (such as lacquer thinner) was applied or painted onto the dried second electrode layer 28 so that the peripheral portion of the alumina paste extends to the partition layer 12 as is depicted in FIG. 9c, and the alumina paste thus applied was air-dried to form an unbaked protective layer 20. Then, the non-baked conditioned multi-layered articled thus produced was baked in air for 2 hours at a temperature of about 1500° C.

EXAMPLE 3

The oxygen sensor 10C of FIG. 4 was produced. For ease of description, the sensor of this example will be designated by 10c -1. The partition layer 12, the first electrolyte layer 26 and the electrolyte layer 16, all being in unbaked condition, were produced by employing the same technique as in the case of the example 1, that is the technique depicted by FIGS. 7a to 7d. A platinum paste composed of 70 wt % powdered platinum and 30 wt % organic medium (such as lacquer thinner) was applied or painted onto the dried electrolyte paste layer 16 in a manner to form a grid-shaped paste heap or layer thereon, as is depicted in FIG. 9a, and at the same time, the platinum paste was applied to the through holes 22c and 22d as shown in FIG. 9b. Then, the platinum paste thus applied was air-dried to form an unbaked second electrode layer 28. The thickness of the layer 28 thus dried was about 6 to 7 μm. Then, an alumina paste composed of 70 wt % powdered alumina and 30 wt % organic medium (such as lacquer thinner) was applied or painted onto the dried second electrode layer 28 so that the peripheral portion of the alumina paste extends to the partition layer 12 as is depicted in FIG. 9c, and the alumina paste was air-dried to form an unbaked protective layer 20. The non-baked conditioned multi-layered article thus produced was baked in air for 2 hours at a temperature of about 1500° C.

EXAMPLE 4

An oxygen sensor having the constructions of the sensor 10A of FIG. 2 and the protective layer 20 was produced. For ease of description, the sensor of this example will be designated by 10A-2. The partition layer 12, the first electrode layer 26 and the electrolyte layer 16, all being in non-baked condition, were produced by employing the same technique as in case of the example 1, that is the technique depicted by FIGS. 7a to 7d. A cermet paste composed of 70 wt % powdered cermet material of 95 wt % Pt and 5 wt % $Y_2O_3$-$ZrO_2$ system (1:19 mole ratio) and 30 wt % organic medium (such as lacquer thinner) was applied or painted onto the non-baked conditioned electrolyte layer 16 in a manner as depicted by FIG. 7e, and at the same time, the cermet paste was applied to the through holes 22c and 22d in a manner as depicted in FIG. 7f. Then, the cermet paste thus applied was air-dried to form an unbaked layer of the second electrode layer 18. The, an unbaked multi-layered article thus produced was baked in air for 2 hours at a temperature of about 1500° C. After this process, powdered calcium zirconate (CaO-$ZrO_2$ system) was deposited on the entire front face of the baked multi-layered article by plasma spraying technique to form a porous protective layer 20, as is depicted by FIG. 7g.

EXAMPLE 5

The oxygen sensor 10C of FIG. 4 was produced. For ease of description, the sensor of this example will be designated by 10C-2. The partition layer 12 in non-baked condition was produced by employing the same technique as in case of the example 1. A cermet paste composed of 70 wt % powdered cermet material of 95 wt % Pt and 5 wt % $Y_2O_3$-$ZrO_2$ system (1:19 mole ratio) and 30 wt % organic medium (such as lacquer thinner) was applied or painted onto the non-baked conditioned partition layer 12 in a manner to form a grid-shaped paste heap or layer thereon as is depicted in FIG. 7c, and the paste heap or layer was air-dried to form an unbaked first electrode layer 26. Then, an electrolyte paste composed of 70 wt % powdered $Y_2O_3$-$ZrO_2$ system (1:19 mole ratio) and 30 wt % organic medium (such as lacquer thinner) was applied or painted onto the dried grid-shaped layer 26 and air-dried to form an unbaked solid electrolyte layer 16, as is depicted by FIG. 7d. Then, the same cermet paste as that forming the first electrode layer 26 was applied or painted onto the dried electrolyte layer 16 in a manner to form a grid-shaped paste heap or layer thereon as is depicted in FIG. 9a, and at the same time, the paste was applied to the through holes 22c and 22d, as is depicted in FIG. 9b. The paste heap or layer was then air-dried to form a non-baked second electrojde layer 28. Then, an alumina paste composed of 70 wt % powdered alumina and 30 wt % organic medium (such as lacquer thinner) was applied or painted onto the dried second elecrode layer 28 and was air-dried to form an unbaked protective layer 20. The unbaked multi-layered article thus produced was baked in air for 2 hours at a temperature of about 1500° C.

CONVENTIONAL OXYGEN SENSOR

Figure 10A:
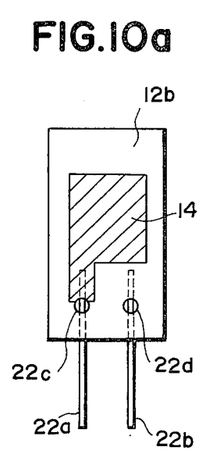
FIGS. 10a to 10d are views depicting, in order, the production process of the conventional oxygen sensor shown in FIG. 1.
Figure 10B:
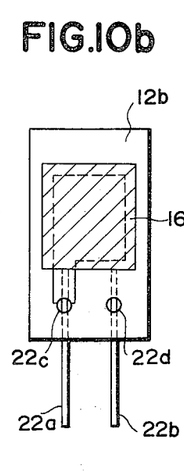
Figure 10C:
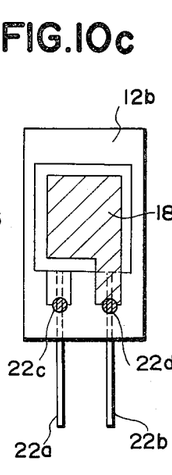
Figure 10D:
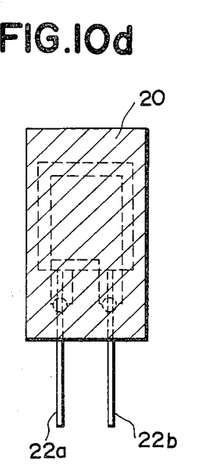

In order to evaluate the oxygen sensors according to the present invention, a conventional oxygen sensor 10 having the construction of FIG. 1 was produced as a comparison article. The production process may become well understood when taken in conjunction with FIGS. 10a to 10d. The partition layer 12 of this conventional sensor was produced by using similar technique to the case of example 1 of the invention. A platinum paste composed of 70 wt % powdered platinum and 30 wt % organic medium (such as lacquer thinner) was applied or painted onto the unbaked partition layer 12 and air-dried to form non-baked first electrode layer 14, the layer 14 having an extension extending to the through hole 22c, as shown in FIG. 10a. The thickness of the layer 14 dried was about 6 to 7 μm. Then, an electrolyte paste composed of 70 wt % powdered $Y_2O_3$-$ZrO_2$ system (1:19 mole ratio) and 30 wt % organic medium (such as lacquer thinner) was applied or painted onto the dried first electrode layer 14 and air-dried to form a non-baked electrolyte layer 16, as depicted in FIG. 10b. The thickness of the dried electrolyte layer 16 was about 10 to 12 μm. Then, the same platinum paste as that forming the first electrode layer 14 was applied or painted onto the dried electrolyte layer 16, forming the layer 18 having an extension extending to the through hole 22d, as shown in FIG. 10c, and at the same time, the platinum paste was applied to the through holes 22c and 22d as shown in FIG. 10c. The platinum paste thus applied to the electrolyte layer 16 was air-dried to form an unbaked second electrolyte layer 18. The thickness of the dried second electrode layer 18 was about 6 to 7 μm. Then, the unbaked multi-layered article thus produced was baked in air for 2 hours at a temperature of 1500° C. After this process, powdered calcium zirconate (CaO-$ZrO_2$ system) was deposited on the entire front face of the baked multi-layered article by plasma spraying technique to from a porous portective layer 20, as is depicted by FIG. 7g.

OXYGEN SENSOR HOLDER FOR EXAMINATION

Figure 8:
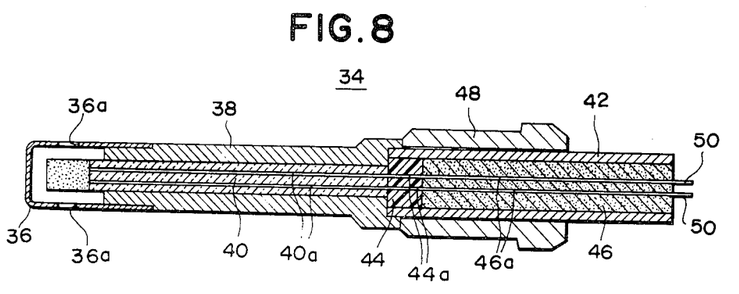
FIG. 8 is a cross section view of a holder which is used for holding the oxygen sensor.

In order to accurately examine the performance and durability of the sensor of the present invention and those of the conventional sensor mentioned above, a holder 34 shown in FIG. 8 was prepared. The holder 34 comprises a stainless steel cap 36 having openings 36a through which a gas subjected to measurement passes. The oxygen sensor to be examined is set in the cap 36. The cap 36 is welded at its open end to an end of a stainless steel tube 38 in which an alumina insulating body 40 is coaxially disposed. The other end of the tube 38 is welded to an end of another stainless steel tube 42 in a manner to be coaxial therewith. Within the tube 42 are disposed a rubber seal 44 and an alumina insulating body 46. Mounted about the tube 42 is a connecting nut 48 which is used for fixing the holder 34 to a suitable member (not shown). Suitable numbers of platinum wires 50 are passed through holes 40a, 44a and 46a formed in the body 40, the rubber seal 44 and the body 46 for electrically connecting the oxygen sensor in the cap 36 with an external measurement unit (not shown).

EXAMINATION 1

The oxygen sensors 10A-1 (example 1), 10B (example 2), 10C-1 (example 3), 10A-2 (example 4) and 10C-2 (example 5) of the invention and the conventional oxygen sensor 10 were subjected to endurance test in an exhaust passage of an automotive internal combustion engine. The test was made on five sample sensors of each kind and these sample sensors were exposed to the exhaust gas emitted from an automotive internal combustion engine under full throttle. The exhaust gas used was richer than stoichiometric (CO=5%) and the temperature of the gas was about 830° C, constantly.

Under this test, it was found that in all samples of the conventional oxygen sensor 10, the first and second electrode layers 14 and 18 respecively had come off or peeled off from their attaching layers within 50 hours from the test start. While, in the samples of the sensors 10B (example 2), 10C-1 (example 3), 10A-2 (example 4) and 10C-2 (example 5), such undersired peeling-off phenomenon was not recognized even when about 150 hours elapsed. The samples of the sensor 10A-1 (example 1) however showed signs of the peeling-off phenomenon at the second electrode layer 18, but at the first electrode layer 26, such phenomenon was not recognized.

EXAMINATION 2

In this examination, the oxygen sensors 10A-1, 10B, 10C-1 10A-2 and 10C-2 of the invention and the conventional oxygen sensor 10 were subjected to endurance test in an exhaust passage of an automobile internal combustion engine. The test was made on five sample sensors of each kind and the sensors were disposed in an exhaust tube of an automotive internal combustion engine which was operated taking alternately a first operation mode of 700 rpm (idling) for 4 minutes and a second operation mode of 4100 rpm for 6 minutes to produce low temperature exhaust gas and high temperature exhaust gas, alternatively. The first operation mode of the engine caused the sensors to be heated at about 400° C., while the second operation mode caused the sensors to be heated at about 800° C.

Under this test, it was found that in all samples of the conventional sensor 10, the first and second electrode layers 14 and 18 respectively had come off or peeled off from the partition layer 12 and the solid electrolyte layer 16, respectively within 100 hours from the test start. While, in the samples of the sensors 10B, 10C-1, 10A-2 and 10C-2, such undesired peeling-off phenomenon was not recognized even when 250-hour test period elapsed. The samples of the oxygen sensor 10A-1 of the invention, however, showed signs of the peeling-off phenomenon at the second electrode layer 18, but at the first electrode layer 26, such phenomenon was not recognized.

It was further found that the oxygen sensors 10A-2 (example 4) and 10C-2 ( example 5), each employing at least one cermet grid-shaped electrode layer, have greater durability than those having platinum grid-shaped electrode layers.

From the aforegoing description, it will be appreciated that using a perforated (or grid-shaped) electrically conducive layer as at least one of the electrode layers of the oxygen sensor permits the sensor to have excellent durability. This is because the mechanical bond between the perforated electrode layer and its neighboring adjacent ceramic layer is reinforced by strong ceramic-ceramic bonds appearing between the adjacent ceramic layers through the openings of the perforated electrode layer.

What is claimed is:

1. An oxygen sensor comprising:
   (a) an oxygen ion conductive solid electrolyte layer;
   (b) an electronically conductive reference electrode layer having a plurality of openings therein, said electrode layer being in intimate contact with one side of said electrolyte layer, said solid electrolyte layer extending through said openings;
   (c) a partition layer of an electrochemically inactive material in intimate contact with the other side of said electrode layer, said electrolyte layer joining said partition layer through said openings in said reference electrode layer;
   (d) an electronically conductive measurement electrode layer in intimate contact with the other side of said electrolyte layer, said measurement electrode layer having a plurality of openings therein;

(e) a porous protective layer in intimate contact with the other side of said measurement electrode layer, said porous protective layer extending through said openings in said measurement electrode layer, said protective layer contacting said electrolyte layer through said openings.

2. An oxygen sensor as claimed in claim 1, in which said reference electrode layer contains therein components of at least one of the solid electrolyte layer and the partition layer.

3. An oxygen sensor as claimed in claim 1, in which said measurement electrode layer contains therein components of at least one of the solid electrolyte layer and the protective layer.

4. An oxygen sensor as claimed in claim 1, further comprising an electrically conductive heating layer embedded in said partition layer.

5. An oxygen sensor as claimed in claim 1, further comprising a DC power source electrically connected between said reference and measurement electrode layers so as to enforcedly cause oxygen ion to flow from one side of said electrolyte layer to the other side of the same.

6. An oxygen sensor as claimed in claim 1, in which said at least one of said reference and measurement electrode layers is in the form of a grid-shaped layer having a plurality of regularly arranged rectangular openings.

* * * * *